United States Patent [19]

Wong et al.

[11] Patent Number: 5,514,784
[45] Date of Patent: May 7, 1996

[54] THIO LINKED GLYCOSYL COMPOUNDS

[76] Inventors: Chi-Huey Wong, Calle Del Alcazar, Rancho Santa Fe, Calif. 92067; Hirosato Kondo, 7502 Charmant, #626, San Diego, Calif. 92122

[21] Appl. No.: 36,334

[22] Filed: Mar. 19, 1993

[51] Int. Cl.$^6$ .......................... C07G 3/00; C07G 11/00; C07H 15/00; C07H 17/00

[52] U.S. Cl. .............................. 536/4.1; 536/18.1

[58] Field of Search .................... 536/4.1, 18.1; 424/1.1

[56] References Cited

U.S. PATENT DOCUMENTS

| | | | |
|---|---|---|---|
| 4,189,471 | 2/1980 | Pon Pipom et al. | 424/88 |
| 4,229,441 | 10/1980 | Bugianesi et al. | 424/182 |
| 4,301,152 | 11/1981 | Ponpipom | 424/182 |
| 4,310,505 | 1/1982 | Baldeschwieler et al. | 424/1 |

*Primary Examiner*—Nathan M. Nutter

[57] ABSTRACT

Thio linked glycosyl compounds are disclosed and synthesized. The synthesis employs a blocked carbohydrate donor and a blocked glycosyl acceptor. The carbohydrate donor includes an acid labile phosphite leaving group attached to the anomeric carbon. The blocked glycosyl acceptor includes an unprotected thio group susceptible to electrophilic attack. The reaction is initiated by the addition of a Lewis acid so as to activate the acid labile phosphite leaving group on the carbohydrate donor. The substitution reaction may be conducted at −78° C. in a solvent such as $Et_3N$ which favors the formation of thio linked glycosylation products.

8 Claims, No Drawings

THIO LINKED GLYCOSYL COMPOUNDS

Government Rights

This invention was made with government support under Grant No. GM 44154 awarded by the National Institutes of Health. The U.S. government has certain rights in the invention.

FIELD OF THE INVENTION

The invention relates to compounds having thio linked glycosyl bonds and to a method for synthesizing such compounds. More particularly, the invention relates to a substitution reaction employing a carbohydrate donor having an acid labile phosphite and an acceptor having an unprotected thio group which is susceptible to electrophilic attack.

BACKGROUND OF THE INVENTION

Simple sugars may be categorized as ketoses or aldoses. When ketoses and aldoses undergo ring closure, they form hemiketals and hemiacetals, respectively. In a hemiketal or hemiacetal, the "carbonyl" carbon is attached to a ring carbon and a ring oxygen. The incorporation of the "carbonyl" carbon into the ring structure of the hemiketal or hemiacetal imparts a new chirality, according to the configuration of the substituents. Accordingly, the "carbonyl" carbon of an aldose or a ketose is termed the "anomeric" carbon.

An oxygen linked glycosyl bond is formed when an anomeric carbon of an hemiacetal or hemiketal is condensed with an alcohol to form a ketal or acetal. The condensation reaction creates a glycosyl bond between the anomeric carbon and the alcohol. If both the hemiacetal or hemiketal and the alcohol are monosaccharides, then the resultant acetal or ketal is a disaccharide. The two subunits of the disaccharide are linked through at least one anomeric carbon by a glycosyl bond.

In an acetal, the anomeric carbon is located at a terminal position on the carbon backbone of the aldose. Accordingly, bond linkages with the anomeric carbon of the acetal include a ring carbon, a ring oxygen, a glycosyl oxygen, and a hydrogen.

In a ketal, the anomeric carbon is centered at a non-terminal carbon within the backbone of the ketose. Accordingly, bond linkages with the anomeric carbon of the ketal include a ring carbon, a ring oxygen, a glycosyl oxygen, and a carbon side chain.

Glycosyl bonds may be formed with or without the assistance of enzyme catalysis. Most natural products having glycosyl bonds are formed with the assistance of enzyme catalysis. A broad array of naturally occurring oligosaccharides and polysaccharides are included within this category. Unfortunately, many oxygen linked glycosyl products are subject to enzymic degradation.

Martin et al. (Tetrahedron Letters (1992), 33 (41), pp 6123– 6126) disclose a non-enzymic method for forming oxygen linked glycosyl bonds. Martin discloses the use of diethyl phosphite as a leaving group for synthesizing oxygen linked glycosyl bonds.

What is needed is an easily synthesized glycosyl bond which can serve as an analog to oxygen linked glycosylation bonds but which does not employ oxygen as a linkage unit.

SUMMARY

The invention is a substitution reaction employed for producing thio linked glycosylation products. The substitution reaction employs a blocked carbohydrate donor and a blocked glycosyl acceptor. The blocked carbohydrate donor includes an anomeric carbon with an acid labile phosphite leaving group attached thereto. An example of a preferred carbohydrate donor is dibenzyl 6-deoxy-2,3,4-tri-O-acetyl-β-L-galactopyranosyl phosphite. The acid labile phosphite leaving group is of a type which is activatable by a Lewis acid. An example of a preferred Lewis acid is trimethylsilyl trifluoromethanesulfonate (TMSOTf). A carbohydrate donor is considered to be "blocked" if it is unreactive with its activated form. The blocked glycosyl acceptor includes an unprotected thio group susceptible to electrophilic substitution. An example of a preferred glycosyl acceptor is p-methoxythiophenol. A glycosyl acceptor is considered to be "blocked" if it is unreactive with the activated carbohydrate donor except at the unprotected thio group.

The blocked carbohydrate donor and blocked glycosyl acceptor are admixed in a solvent which promotes the formation of the substitution glycosylation reaction. An example of a preferred solvent is Et₃N. The reaction is initiated by the addition of the Lewis acid so as to activate the phosphite leaving group on the donor. The activated donor then reacts with the activated acceptor by means of electrophilic attack to produce a thio linked glycosyl bond. After completion, the reaction is then quenched. Quenching may be achieved by washing the glycosylation products with saturated NaHCO₃.

The invention also includes thio linked glycosylation products produced by the above synthetic method. Examples of preferred thio linked glycosylation products include p-methoxyphenyl 6-deoxy-1-thio-β-L-galactopyranose and p-methoxyphenyl 6-deoxy-2,3,4-tri-O-acetyl-1-thio-β-L-galactopyranose.

In an alternative embodiment the method of the invention is employed to synthesize thioglycosylated peptides, i.e. peptides thioglycosidically bonded to carbohydrate through a cysteine sulphydryl group. In such instances, the glycosyl acceptor is a blocked peptide having an unprotected sulphydryl group, e.g. N-benzyloxycarbonyl-L-alanyl-L-cysteine methyl ester.

DETAILED DESCRIPTION

A scheme illustrating a thio linked glycosylation reaction is provided below:

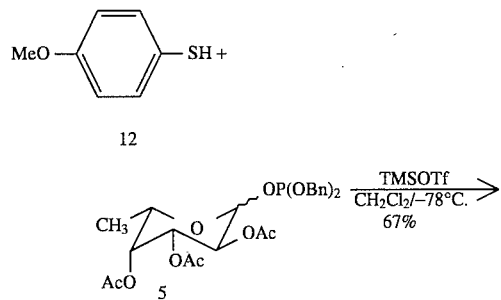

-continued

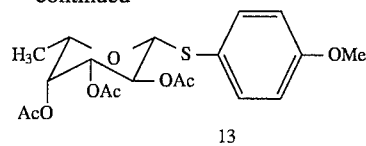

13

EXAMPLE

The blocked glycosyl acceptor, p-methoxythiophenol 12, was purchased from Sigma Chemical Company (St. Louis, Mo.). The blocked carbohydrate donor, dibenzyl 2,3,4-tri-O-acetyl-L-fucosyl phosphite 5 was made according to the method of Ichikawa et al. (J. Org. Chem. 1992, 57, 2943). The blocked glycosyl acceptor 12 (5 mg, 0,036 mmol) and the carbohydrate donor 5 (20 mg, 0.037 mmol) were admixed in 1 mL $CH_2Cl_2$ with molecular sieves of approximately 3 Å and cooled to −78° C. The acid labile dibenzyl phosphite leaving group on the carbohydrate donor 5 was then activated by the addition of a Lewis acid, e.g. 9 mg, 0.040 mmol of trimethylsilyl trifluoromethanesulfonate (TMSOTf). After stirring the admixture for one hour at −78° C., the reaction was quenched with $Et_3N$ and washed with saturated $NaHCO_3$. The organic solvents were dried over $Na_2SO_4$, filtered, and concentrated under reduced pressure.

The resultant residue was separated by preparative thin layer chromatography (Merck Art 5744, AcOEt/Hexane, 2:3) to give the thio linked glycosylation product 13, i.e. p-methoxyphenyl 6-deoxy- 2,3,4-tri-O-acetyl-1-thio-β-L-galactopyranose. The yield was 67% (10 mg). The product 13 appeared as a colorless oil. If desired, the glycosylation product 13 may be de-acetylated to produce p-methoxyphenyl 6-deoxy- 1-thio-β-L-galactopyranose.

The product 13 was subjected to NMR analysis, viz.: $^1H$-NMR ($CDCL_3$) δ; 1.23 (1H, d, J 6.4 Hz, Fuc-$CH_3$), 1.97, 2.10, 2.14 (3H, each s, OAc), 2.34 (3H, s, Ph-$CH_3$), 3.80 (1H, q, J 6.4 HZ, H-5), 4.63 (1H, d, J 9.92 Hz, H-1), 5.03 (1H, dd, J 3.32 9.92 Hz H-3), 5.20 (1H, t, J 9.92 Hz, H-2), 5.25 (1H, dd, J 0.72, 3.22 Hz, H- 4), 7.30 (2H, d, J 7.92 Hz, phenyl protons), 7.416 (2H, d, J 8.10 Hz, phenyl protons).

HRMS: Calclated for $C_{19}H_{24}O_7Cs$ ($M+Cs^+$) 529.0252; found value was 529.0250.

What is claimed is:

1. A substitution reaction for producing thio linked glycosylation products comprising the following steps:
Step A: providing a blocked carbohydrate donor having an anomeric carbon with an acid labile phosphite leaving group attached thereto;
Step B: providing a blocked glycosyl acceptor having an unprotected thio group susceptible to electrophilic substitution, the blocked glycosyl acceptor being p-methoxythiophenol;
Step C: providing a promotor having Lewis acid activity for catalyzing the phosphite leaving group of said Step A; then
Step D: reacting the blocked carbohydrate donor of said Step A with the blocked glycosyl acceptor of said Step B in the presence of the promotor of said Step C within a solvent favoring the formation of thio linked glycosylation products; and then Step E: quenching the reaction of said Step D.

2. A substitution reaction for producing thio linked glycosylation products comprising the following steps:
Step A: providing a blocked carbohydrate donor having an anomeric carbon with an acid labile phosphite leaving group attached thereto;
Step B: providing a blocked glycosyl acceptor having an unprotected thio group susceptible to electrophilic substitution;
Step C: providing a promotor having Lewis acid activity for catalyzing the phosphite leaving group of said Step A, the promotor being trimethylsilyl trifluoromethanesulfonate (TMSOTf); then
Step D: reacting the blocked carbohydrate donor of said Step with the blocked glycosyl acceptor of said Step B in the presence of the promotor of said Step C within a solvent favoring the formation of thio linked glycosylation products; and then
Step E: quenching the reaction of said Step D.

3. A substitution reaction for producing thio linked glycosylation products comprising the following steps:
Step A: providing a blocked carbohydrate donor having an anomeric carbon with an acid labile phosphite leaving group attached thereto;
Step B: providing a blocked glycosyl acceptor having an unprotected thio group susceptible to electrophilic substitution;
Step C: providing a promotor having Lewis acid activity for catalyzing the phosphite leaving group of said Step A; then
Step D: reacting the blocked carbohydrate donor of said Step A with the blocked glycosyl acceptor of said Step B in the presence of the promotor of said Step C within a solvent favoring the formation of thio linked glycosylation products; and then
Step E: quenching the reaction of said Step D by the addition of $Et_3N$ and followed by washing the glycosylation products with saturated $NaHCO_3$.

4. A substitution reaction for producing thio linked glycosylation products comprising the following steps:
Step A: providing a blocked carbohydrate donor having an anomeric carbon with an acid labile phosphite leaving group attached thereto, the phosphite leaving group being dibenzyl phosphite;
Step B: providing a blocked glycosyl acceptor having an protected thio group susceptible to electrophilic substitution;
Step C: providing a promotor having Lewis acid activity for catalyzing the phosphite leaving group of said Step A; then
Step D: reacting the blocked carbohydrate donor of said Step A with the blocked glycosyl acceptor of said Step B in the presence of the promotor of said Step C within a solvent favoring the formation of thio linked glycosylation products; and then
Step E: quenching the reaction of said Step D.

5. A substitution reaction as described in claim 4 wherein:
in said Step A, the blocked carbohydrate donor is dibenzyl 6-deoxy- 2,3,4-tri-O-acetyl-β-L-galactopyranosyl phosphite.

6. A substitution reaction as described in claim 5 wherein:

in said Step A, the blocked carbohydrate donor is dibenzyl 6-deoxy- 2,3,4-tri-O-acetyl-β-L-galactopyranosyl phosphite;

in said Step B, the blocked glycosyl acceptor is p-methoxythiophenol;

in said Step C, the promotor is trimethylsilyl trifluoromethanesulfonate (TMSOTf);

in said step D, the solvent is $CH_2Cl_2$ having a temperature of approximately −78° C. and includes molecular sieves of approximately 3 Å; and in said Step E, quenching is achieved by the addition of $Et_3N$ and is followed by washing the glycosylation products with saturated $NaHCO_3$.

7. p-Methoxyphenyl 6-deoxy-1-thio-β-L-galactopyranose.

8. p-Methoxyphenyl 6-deoxy-2,3,4-tri-O-acetyl-1-thio-β-L-galactopyranose.

* * * * *